US012788712B2

(12) United States Patent
Matsuda et al.

(10) Patent No.: US 12,788,712 B2
(45) Date of Patent: Nov. 10, 2026

(54) INJECTABLE FORMULATIONS OF IBUDILAST

(71) Applicant: MediciNova, Inc., La Jolla, CA (US)

(72) Inventors: Kazuko Matsuda, La Jolla, CA (US); Federico Carlos Aréjola Gaeta, Torremolinos (ES); Yuichi Iwaki, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 455 days.

(21) Appl. No.: 18/221,185

(22) Filed: Jul. 12, 2023

(65) Prior Publication Data

US 2024/0016729 A1 Jan. 18, 2024

Related U.S. Application Data

(60) Provisional application No. 63/388,834, filed on Jul. 13, 2022.

(51) Int. Cl.

| | |
|---|---|
| ***A61K 9/00*** | (2006.01) |
| ***A61K 31/437*** | (2006.01) |
| ***A61K 47/02*** | (2006.01) |
| ***A61K 47/40*** | (2006.01) |
| ***A61K 47/44*** | (2017.01) |

(52) U.S. Cl.

CPC .......... *A61K 9/0019* (2013.01); *A61K 31/437* (2013.01); *A61K 47/02* (2013.01); *A61K 47/40* (2013.01); *A61K 47/44* (2013.01)

(58) Field of Classification Search

CPC .... A61K 9/0019; A61K 31/437; A61K 47/02; A61K 47/40; A61K 47/44

See application file for complete search history.

(56) References Cited

U.S. PATENT DOCUMENTS

| | | | | |
|---|---|---|---|---|
| 6,395,747 | B1 | 5/2002 | Sakoda et al. | |
| 8,138,201 | B2 | 3/2012 | Kalafer et al. | |
| 9,314,452 | B2 | 4/2016 | Kalafer et al. | |
| 2006/0160843 | A1 | 7/2006 | Johnson et al. | |
| 2019/0247369 | A1 * | 8/2019 | Matsuda | A61P 35/00 |
| 2021/0308109 | A1 | 10/2021 | Iwaki et al. | |

FOREIGN PATENT DOCUMENTS

| | | | | |
|---|---|---|---|---|
| WO | WO-2006/063048 | A2 | 6/2006 | |
| WO | WO-2018208723 | A1 * | 11/2018 | A61K 31/4422 |
| WO | WO-2019/147824 | A1 | 8/2019 | |

OTHER PUBLICATIONS

Ghate et al. (Utility of Sulfobutyl Ether β-Cyclodextrin Inclusion Complexes in Drug Delivery: A Review), Indian Journal of Pharmaceutical Sciences, (2019).*

International Search Report and Written Opinion issued in International Patent Application No. PCT/US2023/027450, dated Oct. 24, 2023.

Cho, et al., "Allosteric Inhibition of Macrophage Migration Inhibitory Factor Revealed by Ibudilast," *PNAS*, vol. 107, No. 25, pp. 11313-11318 (2010).

Gibson et al., "The Inhibitory Profile of Ibudilast Against the Human Phosphodiesterase Enzyme Family," European Journal of Pharmacology, vol. 538, pp. 39-42 (2006).

Sanftner et al., "Cross-species comparisons of the pharmacokinetics of ibudilast," Xenobiotica, vol. 39, No. 12, pp. 964-977 (Nov. 2009). [Abstract].

Obernolte, R., et al. (1993) "The cDNA of a human lymphocyte cyclic-AMP phosphodiesterase (PDE IV) reveals a multigene family" Gene 129: 239-247.

Rile et al., "Potentiation of Ibudilast Inhibition of Platelet Aggregation in the Presence of Endothelial Cells," Thrombosis Research, 102 239-246 (2001). [Abstract].

Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).

Suzumura et al., "Ibudilast suppresses TNF.alpha production by glial cells functioning mainly as type III phosphodiesterase inhibitor in NCS," Brain Research, 837:203-212 (1999).

Takuma et al., "Ibudilast attenuates actrocyte apoptsis via cyclic GMP signaling pathway in an in vitro reperfusion model," British Journal of Pharmacology, 133:841-848 (2001).

Yang, et al., "The Emerging Role of Toll-Like Receptor 4 in Myocardial Inflammation," *Cell Death and Disease*, vol. 7 e2234, 10 pages (2016).

Mizuno et al., "Neuroprotective role of phosphodiesterase inhibitor ibudilast on neuronal cell death induced by activated microglia," Neuropharmacology, vol. 46, pp. 404-411 (2004).

* cited by examiner

*Primary Examiner* — Zohreh A Fay

(74) *Attorney, Agent, or Firm* — Foley & Lardner LLP

(57) ABSTRACT

A injectable pharmaceutical compositions consists of a buffered aqueous solution comprising (a) about 5% w/v to about 15% w/v sulfobutylether-β-cyclodextrin (SBE-β-CD), and about 0.05% w/v to about 0.5% w/v ibudilast, or (b) about 5% w/v to about 25% w/v polyoxyl castor oil, and about 1% w/v to about 5% w/v ibudilast.

8 Claims, No Drawings

INJECTABLE FORMULATIONS OF IBUDILAST

CROSS-REFERENCE TO RELATED APPLICATIONS

This application claims the benefit of priority to U.S. Provisional Application No. 63/388,834, filed on Jul. 13, 2022, the contents of which are incorporated by reference herein in their entirety.

BACKGROUND

The small molecule ibudilast (3-isobutyryl-2-isopropylpyrazolo[1,5-a]pyridine) is an inhibitor of macrophage inhibitory factor (MIF) (Cho et al., PNAS-USA, 2010 June 107: 11313-8), is a selective inhibitor of cyclic nucleotide phosphodiesterases (PDEs) 3A, 4, 10A1 and 11A1 (Gibson et al., Eur. J. Pharmacol., 538: 39-42, 2006), and has toll-like receptor-4 (TLR4) antagonistic activity (Yang et al., Cell Death and Disease (2016) 7, e2234; doi:10.1038/cddis.2016.140). Ibudilast distributes well to the CNS (Sanftner et al., Xenobiotica, 2009 39: 964-977) and at clinically-relevant plasma or CNS concentrations, ibudilast selectively inhibits macrophage migration inhibitory factor (MIF) and, secondarily, PDEs 3, 4, 10 and 11. Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News. Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 2006/0160843 discloses ibudilast for the treatment of intermittent and short term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

In advanced stages of disease, a patient may be unable to swallow pills, thus limiting their pharmacotherapy options. An injectable formulation of ibudilast is highly desirable and would improve dosing, until the patient is able to receive oral doses of ibudilast. The technology disclosed herein meets this need.

SUMMARY

Provided herein in one aspect is a pharmaceutical composition is a pharmaceutical composition consisting of a buffered aqueous solution comprising about 5% w/v to about 15% w/v sulfobutylether-β-cyclodextrin (SBE-β-CD), and about 0.05% w/v to about 0.5% w/v ibudilast. In some embodiments, the buffered aqueous solution comprises disodium phosphate ($Na_2HPO_4$) and sodium dihydrogen phosphate ($NaH_2PO_4$). In some embodiments, the $Na_2HPO_4$ is present in the buffered aqueous solution in an amount of about 0.2% w/v and the $NaH_2PO_4$ is present in the buffered aqueous solution in an amount of about 0.06% w/v. In some embodiments, the SBE-β-CD is present in the buffered aqueous solution in an amount of about 10% w/v. In some embodiments, the ibudilast is present in the buffered aqueous solution in an amount of about 0.1% w/v.

Provided herein in another aspect is a pharmaceutical composition consisting of about 10% w/v SBE-β-CD; about 0.2% w/v disodium phosphate; about 0.06% w/v sodium dihydrogen phosphate; about 0.1% w/v ibudilast; and q.s. water.

Provided herein in another aspect is a pharmaceutical composition consisting of a buffered aqueous solution comprising about 5% w/v to about 25% w/v polyoxyl castor oil, and about 1% w/v to about 5% w/v ibudilast. In some embodiments, the buffered aqueous solution comprises about 10% w/v to about 20% w/v polyoxyl castor oil. In some embodiments, the buffered aqueous solution further comprises about 20% w/v to about 60% w/v propylene glycol. In some embodiments, the propylene glycol is present in the buffered aqueous solution in an amount of about 40% w/v. In some embodiments, the polyoxyl castor oil is polyoxyl-35 castor oil. In some embodiments, the buffered aqueous solution comprises disodium phosphate ($Na_2HPO_4$) and sodium dihydrogen phosphate ($NaH_2PO_4$). In some embodiments, the $Na_2HPO_4$ is present in the buffered aqueous solution in an amount of about 0.2% w/v and the $NaH_2PO_4$ is present in the buffered aqueous solution in an amount of about 0.06% w/v. In some embodiments, the ibudilast is present in the buffered aqueous solution in an amount of about 2% w/v. In some embodiments, the pharmaceutical composition is an injectable composition.

Provided herein in another aspect is a pharmaceutical composition consisting of: about 10% w/v polyoxyl castor oil; about 40% w/v propylene glycol; about 0.2% w/v disodium phosphate; about 0.06% w/v sodium dihydrogen phosphate; about 2% w/v ibudilast; and q.s. water. In some embodiments, the pharmaceutical composition is an injectable composition.

Provided herein in another aspect is a pharmaceutical composition consisting of: about 20% w/v polyoxyl castor oil; about 0.2% w/v disodium phosphate; about 0.06% w/v sodium dihydrogen phosphate; about 2% w/v ibudilast; and q.s. water. In some embodiments, the pharmaceutical composition is an injectable composition.

Provided herein in another aspect is a method of treating a neurodegenerative disease or disorder in a subject in need thereof, the method comprising administering to the subject a therapeutically effective amount of a pharmaceutical composition disclosed herein. In some embodiments, the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproteinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis multiplex congenital, or progressive juvenile bulbar palsy (Fazio-Londe), infantile (Werdnig-Hoffman disease), childhood onset, or adolescent (Wohlfart-Kugelberg-Welander disease), degenerative cervical myelopathy, familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

Provided herein in another aspect is a method of treating cancer in a subject in need thereof, the method comprising administering to the subject a therapeutically effective amount of a pharmaceutical composition disclosed herein.

Provided herein in another aspect is a method of preventing metastasis of a cancer in a subject in need thereof, the method comprising administering to the subject a therapeutically effective amount of a pharmaceutical composition disclosed herein.

Provided herein in another aspect is a method of ameliorating metastasis of a cancer in a subject in need thereof, the method comprising administering to the subject a therapeutically effective amount of a pharmaceutical composition disclosed herein.

Provided herein in another aspect is a method of minimizing metastasis of a cancer in a subject in need thereof, the method comprising administering to the subject a therapeutically effective amount of a pharmaceutical composition disclosed herein.

Provided herein in another aspect is a method of preventing relapse of a cancer in a subject in need thereof, the method comprising administering to the subject a therapeutically effective amount of a pharmaceutical composition disclosed herein.

Provided herein in another aspect is a method of ameliorating relapse of a cancer in a subject in need thereof, the method comprising administering to the subject a therapeutically effective amount of a pharmaceutical composition disclosed herein.

Provided herein in another aspect is a method of minimizing risk of relapse or delaying relapse of a cancer in a subject in need thereof, the method comprising administering to the subject a therapeutically effective amount of a pharmaceutical composition disclosed herein.

In some embodiments, the cancer is:

a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, and a vascular tumor;

b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, and mesothelioma;

c. a cancer of the gastrointestinal system selected from squamous cell carcinoma, adenocarcinoma, leiomyosarcoma, lymphoma, carcinoma, ductal adenocarcinoma, insulinoma, glucagonoma, gastrinoma, carcinoid tumors, vipoma, adenocarcinoma, carcinoid tumors, Karposi's sarcoma, hemangioma, lipoma, neurofibroma, fibroma, tubular adenoma, villous adenoma, hamartoma, and leiomyoma;

d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, and lipoma;

e. a cancer of the hepatobiliary and pancreatic system selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, pancreatic exocrine tumor, and pancreatic neuroendocrine tumor;

f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, and sarcoma;

h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, uterine cancer, penile cancer, prostate cancer, and testicular cancer;

i. cancer of the hematologic system selected from myeloid, acute lymphoblastic leukemia, chronic lymphocytic leukemia, myeloproliferative diseases, multiple myeloma, myelodysplastic syndrome, Hodgkin's disease, and non-Hodgkin's lymphoma;

j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, and cancer of the hypopharynx;

k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma, and keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, and secondary malignant neoplasm of other sites.

Provided herein in another aspect is a method of treating an autoimmune disorder in a subject in need thereof, the method comprising administering to the subject a therapeutically effective amount of a pharmaceutical composition disclosed herein. In some embodiments, the autoimmune disorder rheumatoid arthritis, IgA nephropathy, vascular disease associated with kidney disease, systemic lupus erythematosus (SLE), Wegener's granulomatosis, relapsing polychondritis, atopic dermatitis, psoriasis, sarcoidosis, Behcet's disease, Vogt-Koyanagi-Harada's disease, uveitis, or idiopathic pulmonary fibrosis.

Provided herein in another aspect is a method of treating a microorganism infection in a subject in need thereof, the method comprising administering to the subject a therapeutically effective amount of a pharmaceutical composition disclosed herein. In some embodiments, the microorganism infection is caused by virus, bacteria, fungus, or any combination of two or more thereof.

Provided herein in another aspect is a method of treating sepsis and/or septic shock in a subject in need thereof, the method comprising administering to the subject a therapeutically effective amount of a pharmaceutical composition disclosed herein.

Provided herein in another aspect is a method of treating severe viral-induced pneumonia in a subject in need thereof, the method comprising administering to the subject a therapeutically effective amount of a pharmaceutical composition disclosed herein. In some embodiments, the severe viral-induced pneumonia is associated with an infection by a respiratory virus. In some embodiments, the respiratory virus is selected from an influenza virus, a respiratory syncytial virus, a coronavirus, a rhinovirus, an adenovirus, and a parainfluenza virus. In some embodiments, the coronavirus is COVID-19.

Provided herein in another aspect is a method of treating mild to severe acute respiratory distress syndrome (ARDS) in a subject in need thereof, the method comprising administering to the subject a therapeutically effective amount of a pharmaceutical composition disclosed herein, and wherein the subject has positive end-expiratory pressure (PEEP)≥5 cm $H_2O$; and $PaO_2/FiO_2<300$ mm Hg. In some embodiments, the subject has positive end-expiratory pressure (PEEP)≥5 cm $H_2O$; and $PaO_2/FiO_2<200$ mm Hg. In some embodiments, the ARDS is associated with an infection by a respiratory virus. In some embodiments, the respiratory virus is selected from an influenza virus, a respiratory syncytial virus, a coronavirus, a rhinovirus, an adenovirus, and a parainfluenza virus. In some embodiments, the coronavirus is COVID-19.

Provided herein in another aspect is a method of treating fragile X syndrome in a subject in need thereof, the method comprising administering to the subject a therapeutically effective amount of a pharmaceutical composition disclosed herein.

Provided herein in another aspect is a method of treating acute lung injury in a subject in need thereof, the method comprising administering to the subject a therapeutically effective amount of the pharmaceutical composition disclosed herein. In some embodiments, the lung injury is induced by aspiration, trauma, pancreatitis, blood transfusion, or smoke or toxic chemical inhalation. In some embodiments, the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof. In some embodiments, the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

DETAILED DESCRIPTION

The practice of the present disclosure will employ, unless otherwise indicated, conventional methods of chemistry, biochemistry, and pharmacology, within the skill of the art. Such techniques are explained fully in the literature. See, e.g., A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description and FIGURES.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like. The term "q.s." is an abbreviation for "quantum satis" and means "as much as is sufficient."

In describing and claiming the present disclosure, the following terminology will be used in accordance with the definitions described below.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent may include ibudilast or a pharmaceutically acceptable salt thereof.

"Substantially" or "essentially" means nearly totally or completely, for instance, 90% or 95% or greater of some given quantity.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets. In some embodiments, subject, individual, or patient is in reference to a human.

The terms "pharmacologically effective amount" or "therapeutically effective amount" of a composition or agent, as provided herein, refer to a nontoxic but sufficient amount of the composition or agent to provide the desired response, such as a reduction or reversal of any disease or disorder described herein. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the term "treatment" or "treating" means any treatment of a disease or condition or associated disorder, in a patient, including inhibiting the disease or condition, that is, arresting or suppressing the development of clinical symptoms. "Treatment" or "treating" also includes arresting the development of or reversing the symptom or symptoms of a disease. For purposes of the various aspects and embodiments of the present disclosure, beneficial or desired clinical results include, but are not limited to, reduction, alleviation, or amelioration of one or more manifestations of or negative effects of any disease or disorder described herein, improvement in one or more clinical outcomes, diminishment of extent of any disease or disorder described herein, delay or slowing of any disease or disorder described herein progression, amelioration, palliation, or stabilization of the any disease or disorder described herein state, and other beneficial results described herein.

In some aspects, the term "treating" refers to an improvement in clinical outcomes. The term "clinical outcome" refers to any clinical observation or measurement relating to a patient's reaction to a therapy.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Described herein are injectable dosage forms of ibudilast. More particularly, the dosage forms are pharmaceutical compositions consisting of a buffered aqueous solution comprising (a) about 5% w/v to about 15% w/v sulfobutylether-β-cyclodextrin (SBE-β-CD), and about 0.05% w/v to about 0.5% w/v ibudilast, or (b) about 5% w/v to about 25% w/v polyoxyl castor oil, and about 1% w/v to about 5% w/v ibudilast.

Ibudilast

The methods of the disclosure are based upon administration of the molecule, ibudilast. Ibudilast is a small molecule drug (molecular weight of 230.3) having the structure shown below.

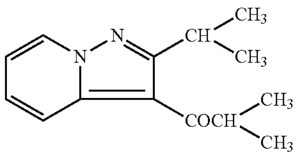

Ibudilast is also found under ChemBank ID 3227, CAS #50847-11-5, and Beilstein Handbook Reference No. 5-24-03-00396. Its molecular formula corresponds to $C_{14}H_{18}N_2O$. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is KETAS®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is an inhibitor of the macrophage inhibitory factor (MIF). Ibudilast is also a selective inhibitor of cyclic nucleotide phosphodiesterases (PDEs) 3A, 4, 10A1 and 11A1 (Gibson et al., Eur. J. Pharmacol. 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: Ca'/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuro-active mediator release. Ibudilast may also suppress the production of pro-inflammatory cytokines (IL-1B, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF-alpha production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848. Ibudilast exhibits good CNS penetration; Sanftner et al. Xenobiotica, (2009) 39: 964-977.

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Pharmaceutical Compositions

In one aspect, described herein are pharmaceutical compositions consisting of a buffered aqueous solution comprising about 5% w/v to about 15% w/v sulfobutylether-β-cyclodextrin (SBE-β-CD), and about 0.05% w/v to about 0.5% w/v ibudilast.

In some embodiments, the buffered aqueous solution comprises about 5%, 6%, 7%, 8%, 9%, 10%, 11%, 12%, 13%, 14%, or 15% w/v SBE-β-CD. In some embodiments, the buffered aqueous solution comprises about 5% w/v to about 13% w/v SBE-β-CD, about 5% w/v to about 11% w/v SBE-β-CD, about 8% w/v to about 15% w/v SBE-β-CD, or about 8% w/v to about 13% w/v SBE-β-CD.

In another aspect, described herein are pharmaceutical compositions consisting of a buffered aqueous solution comprising about 5% w/v to about 25% w/v polyoxyl castor oil, and about 1% w/v to about 5% w/v ibudilast.

In some embodiments, the buffered aqueous solution comprises about 5%, 6%, 7%, 8%, 9%, 10%, 11%, 12%, 13%, 14%, 15%, 16%, 17%, 18%, 19%, 20%, 21%, 22%, 23%, 24%, or 25% w/v polyoxyl castor oil. In some embodiments, the buffered aqueous solution comprises about 5% w/v to about 20% w/v polyoxyl castor oil. In some embodiments, the buffered aqueous solution comprises about 10% w/v to about 20% w/v polyoxyl castor oil. In some embodiments, the buffered aqueous solution comprises about 10% w/v to about 25% w/v polyoxyl castor oil.

In some embodiments, the polyoxyl castor oil is polyoxyl-35 castor oil.

In some embodiments, the buffered aqueous solution further comprises about 20% w/v to about 60% w/v propylene glycol. This includes about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% w/v propylene glycol. In some embodiments, the buffered aqueous solution further comprises about 20% w/v to about 55% w/v, about 20% w/v to about 50% w/v, about 20% w/v to about 45% w/v, about 20% w/v to about 40% w/v, about 20% w/v to about 35% w/v, about 20% w/v to about 30% w/v, about 25% w/v to about 60% w/v, about 25% w/v to about 55% w/v, about 25% w/v to about 50% w/v, about 25% w/v to about 45% w/v, about 25% w/v to about 40% w/v, about 25% w/v to about 35% w/v, about 30% w/v to about 60% w/v, about 30% w/v to about 55% w/v, about 30% w/v to about 50% w/v, about 30% w/v to about 45% w/v, or about 30% w/v to about 40% w/v propylene glycol.

In some embodiments, the buffered aqueous solution comprises disodium phosphate ($Na_2HPO_4$) and sodium dihydrogen phosphate ($NaH_2PO_4$). In some embodiments, the $Na_2HPO_4$ is present in the buffered aqueous solution in an amount of about 0.2% w/v and the $NaH_2PO_4$ is present in the buffered aqueous solution in an amount of about 0.06% w/v.

In some embodiments, the ibudilast is present in the buffered aqueous solution in an amount of about 0.05%, 0.06%, 0.07%, 0.08%, 0.09%, 0.1%, 0.11%, 0.12%, 0.13%, 0.14%, 0.16%, 0.17%, 0.18%, 0.19%, 0.2%, 0.21%, 0.22%, 0.23%, 0.24%, 0.25%, 0.26%, 0.28%, 0.29%, 0.3%, 0.31%, 0.32%, 0.33%, 0.34%, 0.35%, 0.36%, 0.37%, 0.38%, 0.4%, 0.41%, 0.42%, 0.43%, 0.44%, 0.45%, 0.46%, 0.47%, 0.48%, 0.49%, or 0.5% w/v, including increments therein. In some embodiments, the ibudilast is present in the buffered aqueous solution in an amount of about 0.05% w/v to about 0.4% w/v, about 0.05% w/v to about w/v, about 0.05% w/v to about 0.2% w/v, about 0.05% w/v to about 0.1% w/v, about 0.1% w/v to about 0.5% w/v, about 0.1% w/v to about 0.4% w/v, about 0.1% w/v to about 0.3% w/v, or about 0.1% w/v to about 0.2% w/v.

In some embodiments, the ibudilast is present in the buffered aqueous solution in an amount of about 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% w/v, including increments therein. In some embodiments, the ibudilast is present in the buffered aqueous solution in an amount of about 1% w/v to about 4% w/v, about 1% w/v to about 3% w/v, about 1% w/v to about 2% w/v, about 2% w/v to about 5% w/v, about 2% w/v to about 4% w/v, or about 2% w/v to about 3% w/v.

In another aspect, described herein is a pharmaceutical composition comprising, consisting essentially of, or consisting of:

about 10% w/v SBE-β-CD;
about 0.2% w/v disodium phosphate;
about 0.06% w/v sodium dihydrogen phosphate;
about 0.1% w/v ibudilast; and
q.s. water.

In another aspect, described herein is a pharmaceutical composition comprising, consisting essentially of, or consisting of:

about 10% w/v polyoxyl castor oil;
about 40% w/v propylene glycol;
about 0.2% w/v disodium phosphate;
about 0.06% w/v sodium dihydrogen phosphate;
about 2% w/v ibudilast; and
q.s. water.

In another aspect, described herein is a pharmaceutical composition comprising, consisting essentially of, or consisting of:

about 20% w/v polyoxyl castor oil;
about 0.2% w/v disodium phosphate;
about 0.06% w/v sodium dihydrogen phosphate;
about 2% w/v ibudilast; and
q.s. water.

Methods of Treatment

In another aspect, any one of the compositions described herein are used to treat any one or more of the diseases or disorders described herein. Accordingly, a method to treat one or more of the diseases or disorders described herein using a therapeutically effective amount of a composition described herein is another aspect of this disclosure.

In some embodiments, the disease or disorder is neurodegenerative disease, hereditary biochemical disorder, progressive neurodegenerative disease, or symptoms thereof. Exemplary neurodegenerative diseases/disorders include, but are not limited to, Alzheimer's disease, Senile dementia of the Alzheimer type, or Pick's disease (lobar atrophy), multiple sclerosis, neurodegenerative diseases that include syndromes combining progressive dementia with other prominent neurologic abnormalities, progressive neurodegenerative disease mainly afflicting adults and including progressive neurodegenerative forms of Huntington's disease, multiple system atrophy combining dementia with ataxia and/or manifestation of Parkinson's disease, progressive supranuclear palsy (Steele-Richardson-Olszewski), diffuse Lewy body disease, or corticodentatinigral degeneration. Additional subjects can be suffering from progressive neurodegenerative disease that mainly afflicts young adults and children and include Hallervorden-Spatz disease and progressive familial myoclonic epilepsy, progressive neurodegenerative disease that includes syndromes of gradually developing abnormalities of posture and movement, or disease that includes paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, or Gilles de la Tourette syndrome, syndromes of progressive ataxia, cerebellar degenerations or spinocerebellar degenerations, cerebellar cortical degeneration or olivopontocerebellar atrophy (OPCA), spinocerebellar degenerations including spinocerebellar degenerations (Friedreich's ataxia and related disorders). Neurodegenerative diseases/disorders include, but are not limited to, central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), or other forms of familial spinal muscular atrophy, primary lateral sclerosis or hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, progressive neurodegenerative diseases that include syndromes of progressive visual loss. Neurodegenerative diseases/disorders include, but are not limited to, pigmentary degeneration of the retina (retinitis pigmentosa), or hereditary optic atrophy (Leber's disease), motor neuron disease and the progressive ataxias; glaucoma; retinal detachment; sporadic progressive neurodegenerative diseases, multifocal motor neuropathy with conduction block, motor neuropathy with paraproteinemia, motor-predominant peripheral neuropathies, olivopontocerebellar atrophy, Azorean (Machado-Joseph) disease, familial progressive neurodegenerative diseases such as familial amyotrophic lateral sclerosis, spinal muscular atrophies, familial spastic paraparesis, hereditary biochemical disorders, arthrogryposis multiplex congenital, or progressive juvenile bulbar palsy (Fazio-Londe). Examples of hereditary biochemical disorders are superoxide dismutase deficiency, hexosaminidase A and B deficiency, or androgen receptor mutation (Kennedy's syndrome). Progressive neurodegenerative diseases can include viral and prion diseases, such as HTL V-1 associated myelopathy, progressive multifocal leukoencephalopathy, Creutzfeldt-Jakob disease, Gerstmann-Straussler-Scheinker disease, kuru, fatal familial insomnia, or Alper's disease.

"Progressive neurodegenerative disease" means any neurodegenerative disease that is in the progressive state (that is, getting worse compared to a baseline level) or has such progressive characteristics. Thus, a progressive state is a worsening of symptoms over time and can be precipitous or gradual. Examples of progressive neurodegenerative diseases include Parkinson's disease, amyotrophic lateral sclerosis, Alzheimer's disease, and progressive forms of multiple sclerosis exclusive of relapse/remitting multiple sclerosis.

In some embodiments, the disease or disorder is an ophthalmic disease/disorder or injury associated with a neurodegenerative disease/disorder or a neuro-ophthalmologic disorder. In some embodiments, the ophthalmic disease/disorder or injury is retinal injury. In some embodiments, the ophthalmic disease/disorder or injury is macular injury. In some embodiments, the ophthalmic disease/disorder or injury is macular thinness. In some embodiments, the neurodegenerative disease/disorder is progressive multiple sclerosis. Exemplary neuro-ophthalmologic disorders include, but are not limited to, papilledema and idiopathic intracranial hypertension (IIH); anterior ischemic optic neuropathy (AION); optic neuritis; ocular motor cranial neuropathy; and Homer syndrome.

In some embodiments, the disease or disorder is alcoholism and depression and/or dysphoric mood. Examples include alcohol use disorder (AUD) that may be accompanied with depression or dysphoric mood. In some embodiments, the depression is mild depression, moderate depression, or severe depression. In some embodiments, the dysphoric mood is higher dysphoric mood, moderate dysphoric mood, or lower dysphoric mood.

In some embodiments, the disease or disorder is glioblastoma, recurrent glioblastoma or its associated symptoms. In some embodiments, the disease or disorder is glioblastoma. In some embodiments, the disease or disorder is recurrent glioblastoma.

For treating glioblastoma or recurrent glioblastoma, in some embodiments, the patient is a human patient. In some embodiments, the patient has extra copies of the epidermal growth factor receptor (EGFR) gene or expresses abnormally high levels of EGFR. In some embodiments, the abnormally high levels of EGRF refers to higher levels of EGRF in a cancer patient relative to lower levels of EGFR in cancer-free individuals. In some embodiments, the patient lacks heterozygosity in chromosome 10. In some embodiments, the patient displays chromosome 7 amplification. In some embodiments, the patient has a mutated gene selected from the group consisting of TP53, PDGFRA, IDH1, PTEN and NF1. In some embodiments, the patient expresses NEFL, GABRA1, SYT1 or SLC12A5.

In some embodiments, the disease or disorder is multiple sclerosis or progressive multiple sclerosis. There are four recognized types of multiple sclerosis: (1) Relapsing/Remitting Multiple Sclerosis (RR multiple sclerosis), (2) Secondary Progressive Multiple Sclerosis (SP multiple sclerosis), (3) Progressive Relapsing Multiple Sclerosis (PR multiple sclerosis), and (4) Primary Progressive Multiple Sclerosis (PP multiple sclerosis). RR multiple sclerosis is not considered to fall within the scope of the claims, but the other forms of multiple sclerosis, i.e., SP multiple sclerosis, PR multiple sclerosis and PP multiple sclerosis are considered to be one aspect of the present invention. In all types of progressive MS, there is a loss of function over time regardless of relapses.

"Relapsing/Remitting Multiple Sclerosis (RR multiple Sclerosis) is characterized by relapses (also known as exacerbations) during which time new symptoms can appear and old ones resurface or worsen. The relapses are followed by periods of remission, during which time the person fully or partially recovers from the deficits acquired during the relapse. Relapses can last for days, weeks or months and recovery can be slow and gradual or almost instantaneous. The vast majority of people presenting with Multiple Sclerosis are first diagnosed with relapsing/remitting. This is typically when they are in their twenties or thirties, though diagnoses much earlier or later are known. Around twice as many women as men present with this variety.

In "Secondary Progressive Multiple Sclerosis (SP multiple Sclerosis), a person who initially had relapsing-remitting multiple Sclerosis begins to develop a gradual deterioration in nerve function, with or without relapses. After a number of years many people who have had relapsing/remitting multiple Sclerosis will pass into a secondary progressive phase of the disease. This is characterized by a gradual worsening of the disease between relapses. In the early phases of Secondary Progressive MS, the person may still experience a few relapses but after a while, these merge into a general progression. People often do not return to their prior level of function after a relapse. People with Secondary Progressive MS may experience good and bad days or weeks, but, apart from some remission following relapsing episodes, have no real recovery. After 10 years, 50% of people with relapsing/remitting multiple sclerosis will have developed secondary progressive. By 25 to 30 years, that FIGURE will have risen to 90%.

"Progressive Relapsing Multiple Sclerosis (PR multiple sclerosis) shows clear progression in the level of disability from the time symptoms first begin, but with episodes of clear relapses that may or may not be associated with some recovery following the acute episode. This form of multiple sclerosis follows a progressive course from onset, punctuated by relapses. There is significant recovery immediately following a relapse but between relapses, there is a gradual worsening of symptoms.

"Primary Progressive Multiple Sclerosis (PP multiple sclerosis) is characterized by a gradual progression of the disease from its onset with no remissions or relapses at all. There may be periods of a leveling off of disease activity and, as with secondary progressive, there may be good and bad days or weeks. PP multiple sclerosis differs from Relapsing/Remitting MS and Secondary Progressive MS in that onset is typically in the late thirties or early forties, men are as likely women to develop it and initial disease activity is in the spinal cord and not in the brain. Primary Progressive multiple sclerosis often migrates into the brain, but is less likely to damage brain areas than relapsing/remitting or secondary progressive—for example, people with Primary Progressive MS are less likely to develop cognitive problems.

In some embodiments, the progressive multiple sclerosis has progressed beyond relapse remitting multiple sclerosis. In some embodiments, the progressive multiple sclerosis is primary progressive multiple sclerosis. In some embodiments, the primary progressive multiple sclerosis is characterized by disease progression from onset, with occasional plateaus and temporary minor improvements allowed, but not distinct relapses. In some embodiments, the progressive multiple sclerosis is secondary progressive multiple sclerosis. In some embodiments, the secondary progressive multiple sclerosis is characterized as an initial relapsing—remitting course, followed by progression, with or without occasional relapses, minor remissions and plateaus.

In some embodiments, the disease or disorder is cancer.

In some embodiments, the disease or disorder is uveal melanoma.

In some embodiments, the disease or disorder is chemotherapy-induced muscle toxicity and/or chemotherapy-induced cardio-toxicity. In some embodiments, the disease or disorder is chemotherapy-induced neuropathy.

In some embodiments, the disease or disorder is fragile X syndrome.

In some embodiments, the disease or disorder is an autoimmune disorder. Non-limiting examples of an autoimmune disorder include rheumatoid arthritis, IgA nephropathy, vascular disease associated with kidney disease, systemic lupus erythematosus (SLE), Wegener's granulomatosis, relapsing polychondritis, atopic dermatitis, psoriasis, sarcoidosis, Behcet's disease, Vogt-Koyanagi-Harada's disease, uveitis, and idiopathic pulmonary fibrosis.

In some embodiments, the disease or disorder is a microorganism infection. In some embodiments, the microorganism infection is caused by virus, bacteria, fungus, or any combination of two or more thereof.

In some embodiments, the disease or disorder is sepsis and/or septic shock.

In some embodiments, the disease or disorder is severe viral-induced pneumonia. In some embodiments, the severe viral-induced pneumonia is associated with an infection by a respiratory virus. In some embodiments, the respiratory virus is selected from an influenza virus, a respiratory syncytial virus, a coronavirus, a rhinovirus, an adenovirus, and a parainfluenza virus. In some embodiments, the coronavirus is COVID-19.

In some embodiments, the disease or disorder is mild to severe acute respiratory distress syndrome (ARDS) wherein the subject has positive end-expiratory pressure (PEEP)≥5 cm $H_2O$; and $PaO_2/FiO_2<300$ mm Hg. In some embodiments, the subject has positive end-expiratory pressure (PEEP)≥5 cm $H_2O$; and $PaO_2/FiO_2<200$ mm Hg. In some embodiments, the ARDS is associated with an infection by a respiratory virus. In some embodiments, the respiratory virus is selected from an influenza virus, a respiratory syncytial virus, a coronavirus, a rhinovirus, an adenovirus, and a parainfluenza virus. In some embodiments, the coronavirus is COVID-19.

In some embodiments, the disease or disorder is acute lung injury. In some embodiments, the lung injury is induced by aspiration, trauma, pancreatitis, blood transfusion, or smoke or toxic chemical inhalation. In some embodiments, the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof. In some embodiments, the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

In some embodiments, the disease or disorder is chemical-induced lung injury. In some embodiments, the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof. In some embodiments, the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

In another aspect, any one of the compositions described herein are used in a method of preventing metastasis of a cancer in a subject in need thereof, the method comprising administering to the subject a therapeutically effective amount of the composition described herein.

In another aspect, any one of the compositions described herein are used in a method of ameliorating metastasis of a cancer in a subject in need thereof, the method comprising administering to the subject a therapeutically effective amount of the composition described herein.

In another aspect, any one of the compositions described herein are used in a method of minimizing metastasis of a cancer in a subject in need thereof, the method comprising administering to the subject a therapeutically effective amount of the composition described herein.

In another aspect, any one of the compositions described herein are used in a method of preventing relapse of a cancer in a subject in need thereof, the method comprising administering to the subject a therapeutically effective amount of the composition described herein.

In another aspect, any one of the compositions described herein are used in a method of ameliorating relapse of a cancer in a subject in need thereof, the method comprising administering to the subject a therapeutically effective amount of the composition described herein.

In another aspect, any one of the compositions described herein are used in a method of minimizing risk of relapse or delaying relapse of a cancer in a subject in need thereof, the method comprising administering to the subject a therapeutically effective amount of the composition described herein.

In another aspect, any one of the compositions described herein are used in a method of suppressing myeloid-derived suppressor cells (MDSCs) in a patient diagnosed with cancer or suffering therefrom, the method comprising administering to the patient a therapeutically effective amount of the composition described herein.

In another aspect, any one of the compositions described herein are used in a method of reducing immune suppression in a patient diagnosed with cancer or suffering therefrom, the method comprising administering to the patient a therapeutically effective amount of the composition described herein.

In another aspect, any one of the compositions described herein are used in a method of reducing regulatory T-cell count in a patient diagnosed with cancer or suffering therefrom, the method comprising administering to the patient a therapeutically effective amount of the composition described herein.

In another aspect, any one of the compositions described herein are used in a method of increasing CD4+ T-cell count in a patient diagnosed with cancer or suffering therefrom, the method comprising administering to the patient a therapeutically effective amount of the composition described herein.

In some embodiments, the cancer is a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, and a vascular tumor; a cancer of the respiratory tract selected from cancer of the nasal cavity and middle ear, cancer of accessory sinuses, cancer of the larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, and mesothelioma; a cancer of the gastrointestinal system selected from squamous cell carcinoma, adenocarcinoma, leiomyosarcoma, lymphoma, carcinoma, leiomyosarcoma, ductal adenocarcinoma, insulinoma, glucagonoma, gastrinoma, carcinoid tumors, vipoma, adenocarcinoma, carcinoid tumors, Karposi's sarcoma, leiomyoma, hemangioma, lipoma, neurofibroma, fibroma, adenocarcinoma, tubular adenoma, villous adenoma, hamartoma, and leiomyoma; a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, and lipoma; a cancer of the hepatobiliary and pancreatic system selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, pancreatic exocrine tumors (e.g., adenocarcinoma, acinar cell carcinoma, intraductal papillary-mucinous neoplasm, mucinous cystic neoplasm with an invasive adenocarcinoma), and pancreatic neuroendocrine tumors (e.g., gastrinoma, glucagonoma, insulinoma, somatostatinoma, VIPoma (vasoactive intestinal peptide), nonfunctional islet cell tumor); a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors; a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, and sarcoma; a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, uterine cancer, penile cancer, prostate cancer, and testicular cancer; a cancer of the hematologic system selected from myeloid, acute lymphoblastic leukemia, chronic lymphocytic leukemia, myeloproliferative diseases, multiple myeloma, myelodysplastic syndrome, Hodgkin's disease, and non-Hodgkin's lymphoma; a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, and cancer of the hypopharynx; a cancer of the skin selected from malignant melanoma, cutaneous melanoma, basal cell carcinoma, squamous cell carcinoma, Karposi's sarcoma, moles dysplastic nevi, lipoma, angioma, dermatofibroma, and keloidal cancer; or a cancer selected from cancer of the adrenal glands, neuroblastoma, cancer of connective and soft tissue, cancer of the retroperitoneum and peritoneum, eye cancer, intraocular melanoma, uveal melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, and secondary malignant neoplasm of other sites. In some embodiments, the cancer is glioblastoma multiforme (GBM). In some embodiments, the cancer is not glioblastoma multiforme (GBM).

In another aspect, any one of the compositions described herein are used in a method of suppressing myeloid-derived suppressor cells (MDSCs) in a patient diagnosed with microorganism infection or suffering therefrom, the method comprising administering to the patient a therapeutically effective amount of the composition described herein.

In another aspect, any one of the compositions described herein are used in a method of reducing immune suppression in a patient diagnosed with microorganism infection or suffering therefrom, the method comprising administering to the patient a therapeutically effective amount of the composition described herein.

In another aspect, any one of the compositions described herein are used in a method of reducing regulatory T-cell count in a patient diagnosed with microorganism infection or suffering therefrom, the method comprising administering to the patient a therapeutically effective amount of the composition described herein.

In another aspect, any one of the compositions described herein are used in a method of increasing CD4+ T-cell count in a patient diagnosed with microorganism infection or suffering therefrom, the method comprising administering to the patient a therapeutically effective amount of the composition described herein.

In another aspect, any one of the compositions described herein are used in a method of suppressing myeloid-derived suppressor cells (MDSCs) in a patient diagnosed with sepsis or suffering therefrom, the method comprising administering to the patient a therapeutically effective amount of the composition described herein.

In another aspect, any one of the compositions described herein are used in a method of reducing immune suppression in a patient diagnosed with sepsis or suffering therefrom, the method comprising administering to the patient a therapeutically effective amount of the composition described herein.

In another aspect, any one of the compositions described herein are used in a method of reducing regulatory T-cell count in a patient diagnosed with sepsis or suffering therefrom, the method comprising administering to the patient a therapeutically effective amount of the composition described herein.

In another aspect, any one of the compositions described herein are used in a method of increasing CD4+ T-cell count in a patient diagnosed with sepsis or suffering therefrom, the method comprising administering to the patient a therapeutically effective amount of the composition described herein.

Methods of Administration

In another aspect, the present disclosure is directed to injectable administration of ibudilast, or a pharmaceutically acceptable salt thereof. In some embodiments, the injectable administration is intravenous administration. In some embodiments, the intravenous administration provides an infusion of ibudilast, or a pharmaceutically acceptable salt thereof. In some embodiments, the intravenous administration provides a bolus of ibudilast, or a pharmaceutically acceptable salt thereof. In some embodiments, the injectable administration is injection subcutaneously, intramuscularly, intrathecally, intraperitoneally, or intraocularly.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast or pharmaceutically acceptable salt thereof will range from a total daily dosage of about.

In some embodiments, the therapeutically effective amount of ibudilast or pharmaceutically acceptable salt thereof is at least about 5 mg, at least about 10 mg, at least about 20 mg, at least about 25 mg, at least about 30 mg, at least about 35 mg, at least about 40 mg, at least about 45 mg, at least about 50 mg, at least about 55 mg, at least about 60 mg, at least about 65 mg, at least about 70 mg, at least about 75 mg, at least about 80 mg, at least about 85 mg, at least about 90 mg, at least about 95 mg, at least about 100 mg, at least about 110 mg, at least about 120 mg, at least about 130 mg, at least about 140 mg, at least about 150 mg, at least about 160 mg, at least about 170 mg, at least about 180 mg, at least about 190 mg, or at least about 200 mg. In some embodiments, the therapeutically effective amount of ibudilast or pharmaceutically acceptable salt thereof is at least about 50 mg.

In some embodiments, the therapeutically effective amount of ibudilast or pharmaceutically acceptable salt thereof is from about 5 mg to about 10 mg, 5 mg to about 20 mg, 5 mg to about 30 mg, 5 mg to about 40 mg, 5 mg to about 50 mg, 5 mg to about 60 mg, 5 mg to about 70 mg, 5 mg to about 80 mg, 5 mg to about 90 mg, 5 mg to about 100 mg, 5 mg to about 150 mg, 5 mg to about 200 mg, 10 mg to about 20 mg, 10 mg to about 30 mg, 10 mg to about 40 mg, 10 mg to about 50 mg, 10 mg to about 60 mg, 10 mg to about 70 mg, 10 mg to about 80 mg, 10 mg to about 90 mg, 10 mg to about 100 mg, 10 mg to about 150 mg, 10 mg to about 200 mg, 20 mg to about 30 mg, 20 mg to about 40 mg, 20 mg to about 50 mg, 20 mg to about 60 mg, 20 mg to about 70 mg, 20 mg to about 80 mg, 20 mg to about 90 mg, 20 mg to about 100 mg, 20 mg to about 250 mg, 20 mg to about 200 mg, 30 mg to about 40 mg, 30 mg to about 50 mg, 30 mg to about 60 mg, 30 mg to about 70 mg, 30 mg to about 80 mg, 30 mg to about 90 mg, 30 mg to about 100 mg, 30 mg to about 250 mg, 30 mg to about 200 mg, 40 mg to about 50 mg, 40 mg to about 60 mg, 40 mg to about 70 mg, 40 mg to about 80 mg, 40 mg to about 90 mg, 40 mg to about 100 mg, 40 mg to about 250 mg, 40 mg to about 200 mg, 50 mg to about 60 mg, 50 mg to about 70 mg, 50 mg to about 80 mg, 50 mg to about 90 mg, 50 mg to about 100 mg, 50 mg to about 250 mg, or 50 mg to about 200 mg. In some embodiments, the therapeutically effective amount of ibudilast or pharmaceutically acceptable salt thereof is from about 10 mg to about 100 mg.

In some embodiments, the therapeutically effective amount of ibudilast or pharmaceutically acceptable salt thereof is about 5 mg, about 10 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, or about 200 mg. In some embodiments, the therapeutically effective amount of ibudilast or pharmaceutically acceptable salt thereof is about 50 mg.

In some embodiments, the therapeutically effective amount of ibudilast or pharmaceutically acceptable salt thereof is at least about 5 mg/day, at least about 10 mg/day, at least about 20 mg/day, at least about 25 mg/day, at least about 30 mg/day, at least about 35 mg/day, at least about 40 mg/day, at least about 45 mg/day, at least about 50 mg/day, at least about 55 mg/day, at least about 60 mg/day, at least about 65 mg/day, at least about 70 mg/day, at least about 75 mg/day, at least about 80 mg/day, at least about 85 mg/day, at least about 90 mg/day, at least about 95 mg/day, at least about 100 mg/day, at least about 110 mg/day, at least about 120 mg/day, at least about 130 mg/day, at least about 140 mg/day, at least about 150 mg/day, at least about 160 mg/day, at least about 170 mg/day, at least about 180 mg/day, at least about 190 mg/day, or at least about 200 mg/day. In some embodiments, the therapeutically effective amount of ibudilast or pharmaceutically acceptable salt thereof is at least about 50 mg/day.

In some embodiments, the therapeutically effective amount of ibudilast or pharmaceutically acceptable salt thereof is from about 5 mg/day to about 10 mg/day, 5 mg/day to about 20 mg/day, 5 mg/day to about 30 mg/day, 5 mg/day to about 40 mg/day, 5 mg/day to about mg/day, 5 mg/day to about 60 mg/day, 5 mg/day to about 70 mg/day, 5 mg/day to about 80 mg/day, 5 mg/day to about 90 mg/day, 5 mg/day to about 100 mg/day, 5 mg/day to about 150 mg/day, 5 mg/day to about 200 mg/day, 10 mg/day to about 20 mg/day, 10 mg/day to about 30 mg/day, 10 mg/day to about 40 mg/day, 10 mg/day to about 50 mg/day, 10 mg/day to about 60 mg/day, 10 mg/day to about 70 mg/day, 10 mg/day to about 80 mg/day, 10 mg/day to about 90 mg/day, 10 mg/day to about 100 mg/day, 10 mg/day to about 150 mg/day, 10 mg/day to about 200 mg/day, 20 mg/day to about 30 mg/day, 20 mg/day to about 40 mg/day, 20 mg/day to about mg/day, 20 mg/day to about 60 mg/day, 20 mg/day to about 70 mg/day, 20 mg/day to about mg/day, 20 mg/day to about 90 mg/day, 20 mg/day to about 100 mg/day, 20 mg/day to about 250 mg/day, 20 mg/day to about 200 mg/day, 30 mg/day to about 40 mg/day, 30 mg/day to about mg/day, 30 mg/day to about 60 mg/day, 30 mg/day to about 70 mg/day, 30 mg/day to about mg/day, 30 mg/day to about 90 mg/day, 30 mg/day to about 100 mg/day, 30 mg/day to about 250 mg/day, 30 mg/day to about 200 mg/day, 40 mg/day to about 50 mg/day, 40 mg/day to about mg/day, 40 mg/day to about 70 mg/day, 40 mg/day to about 80 mg/day, 40 mg/day to about mg/day, 40 mg/day to about 100 mg/day, 40 mg/day to about 250 mg/day, 40 mg/day to about 200 mg/day, 50 mg/day to about 60 mg/day, 50 mg/day to about 70 mg/day, 50 mg/day to about mg/day, 50 mg/day to about 90 mg/day, 50 mg/day to about 100 mg/day, 50 mg/day to about 250 mg/day, or 50 mg/day to about 200 mg/day. In some embodiments, the therapeutically effective amount of ibudilast or pharmaceutically acceptable salt thereof is from about 10 mg/day to about 100 mg/day.

In some embodiments, the therapeutically effective amount of ibudilast or pharmaceutically acceptable salt thereof is about 5 mg/day, about 10 mg/day, about 20 mg/day, about 25 mg/day, about 30 mg/day, about 35 mg/day, about 40 mg/day, about 45 mg/day, about mg/day, about 55 mg/day, about 60 mg/day, about 65 mg/day, about 70 mg/day, about 75 mg/day, about 80 mg/day, about 85 mg/day, about 90 mg/day, about 95 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, or about 200 mg/day. In some embodiments, the therapeutically effective amount of ibudilast or pharmaceutically acceptable salt thereof is about 50 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from about 1-8 weeks, from 1-12 weeks, from 1-16 weeks, from 1-20 weeks, from 1-24 weeks, from 1-36 weeks, from 1-48 weeks, from 1-52 weeks, from 1-60 weeks, from 1-72 weeks, from 1-84 weeks, from 1-96 weeks, from 1 week to 1 year, from 1 week to 2 years, from 1 week to 3 years, from 1 week to 4 years, from 1 week to 5 years, or longer. In some embodiments, the dosing regimen is for a period of at least about 12, 24, 36, 48, 60, 72, 84, or 96 weeks. In some embodiments, the dosing regimen is for a period of about 12, 24, 36, 48, 60, 72, 84, or 96 weeks. In some embodiments, the dosing regimen is for a period of at least about 1 year, 2 years, 3 years, 4 years, or 5 years. In some embodiments, the dosing regimen is for a period of about 1 year, 2 years, 3 years, 4 years, or 5 years.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Other Actives

A formulation (or kit) in accordance with the disclosure may contain, in addition to ibudilast or a pharmaceutically acceptable salt thereof, one or more additional active agents. In some embodiments, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

Kits

Also provided herein is a kit containing any one of the compositions of the disclosure, accompanied by instructions for use.

For example, the kit comprises ibudilast, or pharmaceutically acceptable salt thereof, along with instructions for use. The ibudilast, or pharmaceutically acceptable salt thereof, and may be packaged in any manner suitable for administration, so long as the packaging, when considered along with the instructions for administration, clearly indicates the manner in which the drug components is to be administered.

For example, in an illustrative kit comprising ibudilast, or pharmaceutically acceptable salt thereof, the kit may be organized by any appropriate time period, such as by day. As an example, for Day 1, a representative kit may comprise unit dosages of each of ibudilast, or pharmaceutically acceptable salt thereof. If each of the drugs is to be administered twice daily, then the kit may contain, corresponding to Day 1, two rows of unit dosage forms of each of ibudilast, or pharmaceutically acceptable salt thereof, along with instructions for the timing of administration. Alternatively, if ibudilast, or pharmaceutically acceptable salt thereof, differ in the timing or quantity of administration, then such would be reflected in the packaging and instructions. Various embodiments according to the above may be readily envisioned, and would of course depend upon the particular combination of drugs, in addition to ibudilast, or pharmaceutically acceptable salt thereof, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister packs, desiccants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

EXAMPLES

Example 1. Initial Solubility Screen with Various Excipients

Solubility of ibudilast was assessed using excipients shown in the following table.

| Entry | Excipients | Concentration (% w/v) | Ibudilast conc. (mg/mL) | Mean solubility (mg/mL) |
|---|---|---|---|---|
| 1 | water | — | 5 | 0.186 |
| 2 | citrate buffer pH 3 | 50 mM | 5 | 0.375 |
| 3 | acetate buffer pH 5 | 50 mM | 5 | 0.175 |
| 4 | phosphate buffer pH 7.5 | 50 mM | 5 | 0.175 |
| 5 | borate buffer pH 9 | 50 mM | 5 | 0.171 |
| 6 | HP-β-CD | 10 | 25 | 2.106 |
| 7 | HP-β-CD | 30 | 25 | 6.721 |
| 8 | SBE-β-CD | 10 | 25 | 3.786 |
| 9 | SBE-β-CD | 30 | 25 | 11.878 |
| 10 | ethanol | 25 | 25 | 4.146 |
| 11 | ethanol* | 100 | 25 | 49.950 |
| 12 | PEG 400 | 25 | 25 | 1.108 |
| 13 | PEG 400* | 100 | 25 | 51.587 |
| 14 | propylene glycol | 25 | 25 | — |
| 15 | propylene glycol* | 100 | 25 | 52.907 |
| 16 | glycerol | 25 | 25 | 0.385 |
| 17 | glycerol | 100 | 25 | 10.297 |
| 18 | Tween 20 | 5 | 25 | 3.205 |
| 19 | Tween 20*** | 50 | 25 | 27.178 |
| 20 | Tween 80 | 5 | 25 | 4.790 |
| 21 | Tween 80 | 30 | 25 | 21.516 |
| 22 | Kolliphor ELP | 5 | 25 | 6.817 |
| 23 | Kolliphor ELP*** | 30 | 25 | 27.986 |
| 24 | Kolliphor HS 15 | 5 | 25 | 5.641 |
| 25 | Kolliphor HS 15 | 50 | 25 | 22.790 |
| 26 | Kolliphor RH 40 | 5 | 25 | 5.585 |
| 27 | Kolliphor RH 40 | 30 | 25 | 29.503 |

*more ibudilast was added up to 50 mg/mL after 2 h tumbling; solubility may be higher
**very viscous; non-reliable data
***fully dissolved after 24 h; solubility may be higher

Example 2. Follow-Up Solubility Assessment

Solubility of ibudilast was assessed using cosolvent mixtures with and without water, increased surfactant concentrations, or a combination of surfactant and cosolvents as shown in the following table.

Concept 1: propylene glycol (500 mg/mL), ethanol (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 2: ethanol (250 mg/mL), glycerol (150 mg/mL), PEG 400 (150 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 3: propylene glycol (400 mg/mL), glycerol (150 mg/mL), PEG 400 (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 4: Kolliphor ELP (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 5: Montanox 80 (300 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL) Concept 6: propylene glycol (500 mg/mL), glycerol (100 mg/mL), Kolliphor ELP (100 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 7: propylene glycol (500 mg/mL), glycerol (100 mg/mL), Montanox 80 (100 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Each solution was prepared at a 50 mL scale using a volumetric flask. Before adding ibudilast, the medium was transferred to a beaker for better homogenization. After ibudilast solubilization, the solution was transferred back into the volumetric flask and water was added to attain the final volume. Final solutions were divided into two 20-mL vials for follow-up at room temperature or at 2-8° C. over several days. A dilution test was performed in 0.9% NaCl solution (2 mL concept formulation diluted in 50 or 100 mL

| Entry | Excipients | Concentration (% w/v) | Ibudilast conc. (mg/mL) | Mean solubility (mg/mL) |
|---|---|---|---|---|
| 1 | propylene glycol/water | 50/50 | 75 | 5.821 |
| 2 | propylene glycol/water | 80/20 | 75 | 37.257 |
| 3 | ethanol/water | 50/50 | 75 | 72.597 |
| 4 | PEG 400/water | 50/50 | 75 | 9.224 |
| 5 | propylene glycol/ethanol/glycerol | 50/25/25 | 75 | 71.923 |
| 6 | propylene glycol/PEG 400/glycerol | 50/25/25 | 75 | 68.661 |
| 7 | propylene glycol/ethanol/water | 50/25/25 | 75 | 71.415 |
| 8 | propylene glycol/PEG 400/water | 50/25/25 | 75 | 31.319 |
| 9 | Tween 80/water | 30/70 | 75 | 31.923 |
| 10 | Tween 80/water* | 80/20 | 75 | 84.406 |
| 11 | Kolliphor ELP/water | 30/70 | 75 | 42.695 |
| 12 | Kolliphor ELP/water* | 80/20 | 75 | 97.646 |
| 13 | Tween 80/propylene glycol/water | 5/50/45 | 75 | 14.781 |
| 14 | Tween 80/propylene glycol/water | 30/50/20 | 75 | 76.292 |
| 15 | Kolliphor ELP/propylene glycol/water | 5/50/45 | 75 | 19.409 |
| 16 | Kolliphor ELP/propylene glycol/water | 30/50/20 | 75 | 72.864 |
| 17 | Tween 80/ethanol/water | 5/50/45 | 75 | 84.040 |
| 18 | Kolliphor ELP/ethanol/water | 5/50/45 | 75 | 83.668 |

*Less than 5 mL added due to viscosity of medium

Example 3. Solution Screening, Part 1

Based on the results from the initial solubility screen and the follow-up solubility assessment, seven formulation concepts were assessed. All seven concepts comprised 25 mg/mL ibudilast and sodium phosphate buffer at 15 mM, targeting pH 7.5.

salt solution). Concepts 1, 2, and 3 were also formulated without buffer to assess impact of buffer on solubility.

Concept 1 (with buffer), Concept 2 (with buffer), Concept 3 (with or without buffer), and concept 5 demonstrated solubility problems during the preparation of the formulations. The remaining concepts were brought forward for dilution testing. Concepts 4 and 6 exhibited a clear solution after dilution in 50 and 100 mL saline solution; the other concepts (concept 1 without buffer, concept 2 without buffer, and concept 7) exhibited solubility issues after dilution testing.

Example 4. Solution Screening, Part 2

Based on the results from the solution screening, part 1, concepts 4 and 6 were more thoroughly examined the potential effect of buffer. Additional concepts (8A, 8B, 9, 10, 11, 12, and 13) involving surfactant with alternative solvent (s) and with or without buffer were also examined.

Concept 4A: Kolliphor ELP (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 4B: Kolliphor ELP (250 mg/mL), ibudilast (25 mg/mL), water (q.s. 1 mL)

Concept 6A: propylene glycol (500 mg/mL), glycerol (100 mg/mL), Kolliphor ELP (100 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 6B: propylene glycol (500 mg/mL), glycerol (100 mg/mL), Kolliphor ELP (100 mg/mL), ibudilast (25 mg/mL), water (q.s. 1 mL)

Concept 8A: ethanol (100 mg/mL), Kolliphor ELP (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 8B: ethanol (100 mg/mL), Kolliphor ELP (250 mg/mL), $Na_2HPO_4$ $2H_2O$ (1.9941 mg/mL), $NaH_2PO_4$ $2H_2O$ (0.5923 mg/mL), ibudilast (25 mg/mL), water (q.s. 1 mL)

Concept 9: Kolliphor ELP (200 mg/mL), $Na_2HPO_4$ $2H_2O$ (1.9941 mg/mL), $NaH_2PO_4$ $2H_2O$ (0.5923 mg/mL), ibudilast (20 mg/mL), water (q.s. 1 mL)

Concept 10: Kolliphor ELP (100 mg/mL), $Na_2HPO_4$ $2H_2O$ (1.9941 mg/mL), $NaH_2PO_4$ $2H_2O$ (0.5923 mg/mL), ibudilast (10 mg/mL), water (q.s. 1 mL)

Concept 11: propylene glycol (500 mg/mL), Kolliphor ELP (100 mg/mL), $Na_2HPO_4$ $2H_2O$ (1.9941 mg/mL), $NaH_2PO_4$ $2H_2O$ (0.5923 mg/mL), ibudilast (20 mg/mL), water (q.s. 1 mL)

Concept 12: propylene glycol (500 mg/mL), Kolliphor ELP (50 mg/mL), $Na_2HPO_4$ $2H_2O$ (1.9941 mg/mL), $NaH_2PO_4$ $2H_2O$ (0.5923 mg/mL), ibudilast (10 mg/mL), water (q.s. 1 mL)

Concept 13: propylene glycol (400 mg/mL), Kolliphor ELP (100 mg/mL), $Na_2HPO_4$ $2H_2O$ (1.9941 mg/mL), $NaH_2PO_4$ $2H_2O$ (0.5923 mg/mL), ibudilast (20 mg/mL), water (q.s. 1 mL)

For concepts 9 and 10 at 50-mL scale: Kolliphor ELP was melted at 55° C. and then weighed in a beaker. Ibudilast was added under magnetic stirring for 1.5 h for both concepts 9 and 10. Heated water (40° C.) was added, and a viscous solution was obtained for concept 9, but a homogenization occurred after only 10 min for concept 10. A buffered solution was added under magnetic stirring until complete homogenization for concept 9 (1.5 h) and for concept 10 (10 min). Solutions were transferred to respective volumetric flasks prior to addition of more water at room temperature to final volume.

For concepts 11, 12, and 13 at 50-mL scale: Kolliphor ELP was melted at 55° C. and then weighed in a beaker. Propylene glycol was added to the beaker, and homogenization occurred under magnetic stirring for a few minutes, resulting in opalescent solutions. Ibudilast was added under magnetic stirring for concept 11 (1 h, opalescent solution), concept 12 (1 h, opalescent solution), and concept 13 (1.5 h, opalescent solution). A buffered solution was added under magnetic stirring at room temperature until complete homogenization for concepts 11, 12, and 13 (10 min each). Solutions were transferred to respective volumetric flasks prior to addition of more water at room temperature to final volume.

Use of Kolliphor ELP in up to 25% water resulted in a very viscous gel which took time to solubilize. Concept 11 had a high viscosity (14.65 mPa s) at t=0, making filtration difficult. Viscosity values of concept 9, 10, 12, and 13 were lower at t=0: 7.33 mPa s (concept 9), 2.12 mPa s (concept 10), 6.60 mPa s (concept 12), and 9.66 mPa s (concept 13). Concept 10 was slightly opalescent at t=0 and at t=20 h, whereas concepts 9, 11, 12, and 13 were clear solutions at t=0 and at t=20 h.

Formulations of concepts 9-13 without buffer were also assessed. Concepts 11-13 without buffer exhibited opalescence which would resolve upon heating although minor precipitation remained.

Concepts 9 and 13, each with 20 mg/mL ibudilast, were examined in further stability studies. Buffered solutions exhibited better pH stability (less than 0.4 pH unit change) over 10 days at various temperatures (2-8° C. or 60° C.) than the non-buffered counterparts (up to 2 pH unit change). Flocculation/precipitation was also observed for concept 9 at t=10 days (60° C.). Three-week stability tests demonstrated similar results.

Example 5. Solution Screening, Part 3

Additional aqueous formulations were evaluated.

Concept 14: SBE-β-CD (100 mg/mL), ibudilast (1 mg/mL), water (q.s. 1 mL)

Concept 15: SBE-β-CD (100 mg/mL), $Na_2HPO_4$ $2H_2O$ (2.0284 mg/mL), $NaH_2PO_4$ $2H_2O$ (0.5622 mg/mL), ibudilast (1 mg/mL), water (q.s. 1 mL)

Concept 16: propylene glycol (3 mg/mL), ethanol (80 mg/mL), ibudilast (1 mg/mL), water (q.s. 1 mL)

Concept 17: PEG 400 (100 mg/mL), ethanol (50 mg/mL), ibudilast (1 mg/mL), water (q.s. 1 mL)

Concept 18: PEG 400 (100 mg/mL), ethanol (30 mg/mL), ibudilast (1 mg/mL), water (q.s. 1 mL)

Concept 19: PEG 400 (100 mg/mL), ethanol (80 mg/mL), ibudilast (1 mg/mL), water (q.s. 1 mL)

Concept 20: PEG 400 (100 mg/mL), ethanol (100 mg/mL), ibudilast (1 mg/mL), water (q.s. 1 mL)

Concept 21: PEG 400 (75 mg/mL), ethanol (100 mg/mL), ibudilast (1 mg/mL), water (q.s. 1 mL)

Concept 22: PEG 400 (150 mg/mL), ethanol (80 mg/mL), ibudilast (1 mg/mL), water (q.s. 1 mL)

Concept 23: PEG 400 (150 mg/mL), ethanol (50 mg/mL), ibudilast (1 mg/mL), water (q.s. 1 mL)

Concept 24: PEG 400 (150 mg/mL), ethanol (100 mg/mL), ibudilast (1 mg/mL), water (q.s. 1 mL)

Concept 25: PEG 400 (100 mg/mL), ethanol (100 mg/mL), $Na_2HPO_4$ $2H_2O$ (2.0284 mg/mL), $NaH_2PO_4$ $2H_2O$ (0.5622 mg/mL), ibudilast (1 mg/mL), water (q.s. 1 mL)

Concept 26: PEG 400 (150 mg/mL), ethanol (100 mg/mL), $Na_2HPO_4$ $2H_2O$ (2.0284 mg/mL), $NaH_2PO_4$ $2H_2O$ (0.5622 mg/mL), ibudilast (1 mg/mL), water (q.s. 1 mL)

Concept 27: PEG 400 (75 mg/mL), ethanol (100 mg/mL), $Na_2HPO_4$ $2H_2O$ (2.0284 mg/mL), $NaH_2PO_4$ $2H_2O$ (0.5622 mg/mL), ibudilast (1 mg/mL), water (q.s. 1 mL)

All the concepts, with a clear solution at TO, were stored for follow up at RT and 2-8° C. Only four concepts were still clear solutions after 48 h and 7 days at both storage temperatures: the two concepts prepared with SBE-β-CD at 10% (concept 15 buffered and concept 14 non buffered), and the two concepts formulated with 10% EtOH and 15% PEG 400 (concept 26 buffered and concept 24 non buffered). All the other concepts started to precipitate after 24 h storage or 48 h storage at 2-8° C. The pH values of the concepts 14, 15, 24 and 26 were all between 6.3 and 8, with the buffered versions having pH values closer to target pH for infusion product (around 7.5).

In regards to osmolality, the two concepts prepared with SBE-β-CD were close to isotonicity with values of 267 mOsm/kg for the non-buffered one (concept 14) and 302 mOsm/kg for the buffered one (concept 15). Osmolality values were higher for the concepts with PEG 400/ethanol co-solvents.

Concepts 14, 15, and 24 were further evaluated in a short stress study to assess their physical and chemical stability during storage at different conditions (i.e., 2-8° C., 25° C./60% RH, 40° C./75% RH and 60° C.) over a period of 4 weeks. A preliminary shear stress study and a freeze/thaw study were also conducted. Concept 15 outperformed concepts 14 and 24.

Example 6. Phase 1, Single Dose, Safety, Tolerability, and Pharmacokinetics Study to Examine Rate and Extent of Absorption of an Extended-Release Oral or a Parenteral Formulation of Ibudilast in Healthy Volunteers Subjects participated in 2 different Parts in this study:

Part A is a crossover, open-label, single-center, Phase 1 study in 12 healthy volunteers. Subjects that met study eligibility and provided informed consent were randomized in two sequences according to one of the following treatments in Part A.

| Sequence | Week 1 | Week 2 | Week 3 |
|---|---|---|---|
| 1 | ERC fed | ERC fasted | IRC fasted |
| 2 | ERC fasted | ERC fed | IRC fasted |

ERC = extended release capsule;
IRC = intermediate-release capsule (commercially available)

Part B: subjects received a single dose of 10 mg ibudilast (formulation according to concept 15) intravenously at consistent rate infusion over 4 hours (1 mg/mL).

During each dosing treatment, subjects checked in to the study facility the night before dosing and remained at the facility until 32 hours after dosing. Subjects returned to the study facility for outpatient visits at each remaining PK sampling day (48, 72, 96, and 168 hours after treatment). Subjects were discharged from the study at 168 hours after the start of study drug infusion.

Blood samples (approximately 2 mL per sample) were collected at pre-dose, 0.5, 1, 2 (end of infusion), 4, 6, 8, 10, 12, 24, 32, 48, 72, 96 and 168 hours after the start of the infusion in each treatment. Blood samples were assayed for ibudilast using a validated liquid chromatography/tandem mass spectroscopy (LC/MS/MS) method.

Pharmacokinetic data was as follows for the intravenous injection:

| | HL_Lambda_z (h) | $T_{max}$ (h) | $C_{max}$ (ng/mL) | $AUC_{last}$ (h*ng/mL) | $AUC_{inf}$_obs (h*ng/mL) | Vz_obs (L) | Cl_obs (L/h) |
|---|---|---|---|---|---|---|---|
| N | 11 | 12 | 12 | 12 | 11 | 11 | 11 |
| Mean | 35.1 | 4.00 | 36.6 | 342 | 432 | 1130 | 34.9 |
| SD | 27.0 | 0.00 | 18.6 | 269 | 298 | 685 | 24.2 |
| Min. | 3.59 | 4.00 | 22.5 | 72.3 | 113 | 460 | 9.87 |
| Median | 33.7 | 4.00 | 31.7 | 310 | 392 | 795 | 25.5 |
| Max. | 81.9 | 4.00 | 90.8 | 961 | 1010 | 2440 | 88.8 |
| CV % | 76.9 | 0.00 | 50.8 | 78.6 | 68.9 | 60.4 | 69.4 |

Pharmacokinetic data was as follows for the intermediate-release capsule (50 mg single dose):

| | HL_Lambda_z (h) | $T_{max}$ (h) | $C_{max}$ (ng/ml) | $AUC_{last}$ (h*ng/ml) | $AUC_{inf}$_obs (h*ng/ml) |
|---|---|---|---|---|---|
| N | 12 | 12 | 12 | 12 | 12 |
| Mean | 27.8 | 4.17 | 73.3 | 761 | 1530 |
| SD | 24.8 | 0.577 | 27.3 | 296 | 807 |
| Min. | 8.95 | 4.00 | 36.4 | 427 | 509 |
| Median | 17.7 | 4.00 | 66.9 | 715 | 1320 |
| Max. | 98.3 | 6.00 | 135 | 1490 | 3360 |
| CV % | 89.3 | 13.9 | 37.3 | 38.9 | 52.9 |

CERTAIN EMBODIMENTS

Embodiment 1. A pharmaceutical composition consisting of a buffered aqueous solution comprising about 5% w/v to about 15% w/v sulfobutylether-β-cyclodextrin (SBE-β-CD), and about 0.05% w/v to about 0.5% w/v ibudilast.

Embodiment 2. The pharmaceutical composition of Embodiment 1, wherein the buffered aqueous solution comprises disodium phosphate ($Na_2HPO_4$) and sodium dihydrogen phosphate ($NaH_2PO_4$).

Embodiment 3. The pharmaceutical composition of Embodiment 2, wherein the $Na_2HPO_4$ is present in the buffered aqueous solution in an amount of about 0.2% w/v and the $NaH_2PO_4$ is present in the buffered aqueous solution in an amount of about 0.06% w/v.

Embodiment 4. The pharmaceutical composition of any one of Embodiments 1-3, wherein the SBE-β-CD is present in the buffered aqueous solution in an amount of about 10% w/v.

Embodiment 5. The pharmaceutical composition of any one of Embodiments 1-4, wherein the ibudilast is present in the buffered aqueous solution in an amount of about 0.1% w/v.

Embodiment 6. A pharmaceutical composition consisting of:

about 10% w/v SBE-β-CD;
about 0.2% w/v disodium phosphate;
about 0.06% w/v sodium dihydrogen phosphate;
about 0.1% w/v ibudilast; and
q.s. water.

Embodiment 7. A pharmaceutical composition consisting of a buffered aqueous solution comprising about 5% w/v to about 25% w/v polyoxyl castor oil, and about 1% w/v to about 5% w/v ibudilast.

Embodiment 8. The pharmaceutical composition of Embodiment 7, wherein the buffered aqueous solution comprises about 10% w/v to about 20% w/v polyoxyl castor oil.

Embodiment 9. The pharmaceutical composition of Embodiment 7 or Embodiment 8, wherein the buffered aqueous solution further comprises about 20% w/v to about 60% w/v propylene glycol.

Embodiment 10. The pharmaceutical composition of Embodiment 9, wherein the propylene glycol is present in the buffered aqueous solution in an amount of about 40% w/v.

Embodiment 11. The pharmaceutical composition of any one of Embodiments 7-10, wherein the polyoxyl castor oil is polyoxyl-35 castor oil.

Embodiment 12. The pharmaceutical composition of any one of Embodiments 7-11, wherein the buffered aqueous solution comprises disodium phosphate ($Na_2HPO_4$) and sodium dihydrogen phosphate ($NaH_2PO_4$).

Embodiment 13. The pharmaceutical composition of Embodiment 12, wherein the $Na_2HPO_4$ is present in the buffered aqueous solution in an amount of about 0.2% w/v and the $NaH_2PO_4$ is present in the buffered aqueous solution in an amount of about 0.06% w/v.

Embodiment 14. The pharmaceutical composition of any one of Embodiments 7-13, wherein the ibudilast is present in the buffered aqueous solution in an amount of about 2% w/v.

Embodiment 15. A pharmaceutical composition consisting of:

about 10% w/v polyoxyl castor oil;
about 40% w/v propylene glycol;
about 0.2% w/v disodium phosphate;
about 0.06% w/v sodium dihydrogen phosphate;
about 2% w/v ibudilast; and
q.s. water.

Embodiment 16. A pharmaceutical composition consisting of:

about 20% w/v polyoxyl castor oil;
about 0.2% w/v disodium phosphate;
about 0.06% w/v sodium dihydrogen phosphate;
about 2% w/v ibudilast; and
q.s. water.

Embodiment 17. The pharmaceutical composition of any one of Embodiments 1-16, wherein the pharmaceutical composition is an injectable composition.

Embodiment 18. A method of treating a neurodegenerative disease or disorder in a subject in need thereof, the method comprising administering to the subject a therapeutically effective amount of the pharmaceutical composition of any one of Embodiments 1-17.

Embodiment 19. The method of Embodiment 18, wherein the neurodegenerative disease or disorder is Alzheimer's disease, Senile dementia of the Alzheimer type, Pick's disease (lobar atrophy), syndromes combining progressive dementia with other prominent neurologic abnormalities, Huntington's disease, multiple system atrophy combining dementia with ataxia and/or manifestation of Parkinson's disease, progressive supranuclear palsy (Steele-Richardson-Olszewski), diffuse Lewy body disease, corticodentatinigral degeneration, Hallervorden-Spatz disease, progressive familial myoclonic epilepsy, symptoms of gradually developing abnormalities of posture and movement, paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, Gilles de la Tourette syndrome, progressive ataxia, cerebellar degenerations, spinocerebellar degenerations, cerebellar cortical degeneration, olivopontocerebellar atrophy (OPCA), spinocerebellar degenerations (Friedreich's ataxia and related disorders), central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), other forms of familial spinal muscular atrophy, primary lateral sclerosis, hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, syndromes of progressive visual loss, pigmentary degeneration of the retina (retinitis pigmentosa), hereditary optic atrophy (Leber's disease), Parkinson's disease and other extrapyramidal disorders, progressive supranuclear palsy (Steele-Richardson-Olszewski syndrome), torsion dystonia (torsion spasm, dystonia musculorum deformans), focal dystonias, motor neuron disease, progressive ataxias, primary lateral sclerosis, multifocal motor neuropathy with conduction block, motor neuropathy with paraproteinemia, motor-predominant peripheral neuropathies, olivopontocerebellar atrophy, Azorean (Machado-Joseph) disease, familial progressive neurodegenerative diseases, familial amyotrophic lateral sclerosis, spinal muscular atrophies, familial spastic paraparesis, hereditary biochemical disorders, arthrogryposis multiplex congenital, or progressive juvenile bulbar palsy (Fazio-Londe), infantile (Werdnig-Hoffman disease), childhood onset, or adolescent (Wohlfart-Kugelberg-Welander disease), degenerative cervical myelopathy, familial HTLV-1 myelopathy, isolated FSP, or complicated FSP, superoxide dismutase deficiency, hexosaminidase A and B deficiency, androgen receptor mutation (Kennedy's syndrome), viral and prion diseases, myelopathy, progressive multifocal leukoencephalopathy, Creutzfeldt-Jakob disease, Gerstmann-Straussler-Scheinker disease, kuru, fatal familial insomnia, Alper's disease, primary progressive or secondary progressive multiple sclerosis, but not relapsing, remitting multiple sclerosis, frontotemporal dementia, Wilson's disease, progressive neuropathic pain, ischemia caused by stroke, traumatic brain injury, or spinal cord injury.

Embodiment 20. A method of treating cancer in a subject in need thereof, the method comprising administering to the subject a therapeutically effective amount of the pharmaceutical composition of any one of Embodiments 1-17.

Embodiment 21. A method of preventing metastasis of a cancer in a subject in need thereof, the method comprising administering to the subject a therapeutically effective amount of the pharmaceutical composition of any one of Embodiments 1-17.

Embodiment 22. A method of ameliorating metastasis of a cancer in a subject in need thereof, the method comprising administering to the subject a therapeutically effective amount of the pharmaceutical composition of any one of Embodiments 1-17.

Embodiment 23. A method of minimizing metastasis of a cancer in a subject in need thereof, the method comprising administering to the subject a therapeutically effective amount of the pharmaceutical composition of any one of Embodiments 1-17.

Embodiment 24. A method of preventing relapse of a cancer in a subject in need thereof, the method comprising administering to the subject a therapeutically effective amount of the pharmaceutical composition of any one of Embodiments 1-17.

Embodiment 25. A method of ameliorating relapse of a cancer in a subject in need thereof, the method comprising administering to the subject a therapeutically effective amount of the pharmaceutical composition of any one of Embodiments 1-17.

Embodiment 26. A method of minimizing risk of relapse or delaying relapse of a cancer in a subject in need thereof, the method comprising administering to the subject a therapeutically effective amount of the pharmaceutical composition of any one of Embodiments 1-17.

Embodiment 27. The method of any one of Embodiments 20-26, wherein the cancer is:

a. a cancer of the circulatory system selected from angiosarcoma, fibrosarcoma, rhabdomyosarcoma, liposarcoma, myxoma, rhabdomyoma, fibroma, lipoma and teratoma, cancer of the mediastinum and pleura, and a vascular tumor;

b. a cancer of the respiratory tract selected from cancer of the nasal cavity and middle ear, cancer of accessory sinuses, cancer of larynx, cancer of the trachea, cancer of the bronchus and lung, small cell lung cancer (SCLC), non-small cell lung cancer (NSCLC), bronchogenic carcinoma, squamous cell carcinoma, undifferentiated small cell carcinoma, undifferentiated large cell carcinoma, adenocarcinoma, alveolar (bronchiolar) carcinoma, bronchial adenoma, sarcoma, lymphoma, chondromatous hamartoma, and mesothelioma;

c. a cancer of the gastrointestinal system selected from squamous cell carcinoma, adenocarcinoma, leiomyosarcoma, lymphoma, carcinoma, ductal adenocarcinoma, insulinoma, glucagonoma, gastrinoma, carcinoid tumors, vipoma, adenocarcinoma, carcinoid tumors, Karposi's sarcoma, hemangioma, lipoma, neurofibroma, fibroma, tubular adenoma, villous adenoma, hamartoma, and leiomyoma;

d. a cancer of the genitourinary tract selected from adenocarcinoma, Wilm's tumor (nephroblastoma), lymphoma, leukemia, squamous cell carcinoma, transitional cell carcinoma, adenocarcinoma, adenocarcinoma, sarcoma of the prostate, seminoma, teratoma, embryonal carcinoma, teratocarcinoma, choriocarcinoma, interstitial cell carcinoma, fibroma, fibroadenoma, adenomatoid tumors, and lipoma;

e. a cancer of the hepatobiliary and pancreatic system selected from hepatoma (hepatocellular carcinoma), cholangiocarcinoma, hepatoblastoma, angiosarcoma, hepatocellular adenoma, hemangioma, pheochromocytoma, insulinoma, vasoactive intestinal peptide tumor, islet cell tumor, pancreatic exocrine tumor, and pancreatic neuroendocrine tumor;

f. a cancer of the bone selected from osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors;

g. a cancer of the nervous system selected from primary CNS lymphoma, osteoma, hemangioma, granuloma, xanthoma, osteitis deformans, meningioma, meningiosarcoma, gliomatosis, astrocytoma, medulloblastoma, glioma, ependymoma, germinoma (pinealoma), oligodendroglioma, schwannoma, retinoblastoma, congenital tumors, spinal cord neurofibroma, meningioma, glioma, and sarcoma;

h. a cancer of the reproductive system selected from endometrial carcinoma, cervical carcinoma, pre-tumor cervical dysplasia, ovarian carcinoma, serous cystadenocarcinoma, mucinous cystadenocarcinoma, unclassified carcinoma, granulosa-thecal cell tumors, Sertoli-Leydig cell tumors, dysgerminoma, malignant teratoma, squamous cell carcinoma of the vulva, intraepithelial carcinoma of the vulva, adenocarcinoma of the vulva, fibrosarcoma of the vulva, melanoma of the vulva, vaginal clear cell carcinoma, vaginal squamous cell carcinoma, vaginal botryoid sarcoma (embryonal rhabdomyosarcoma), carcinoma of the fallopian tubes placental cancer, uterine cancer, penile cancer, prostate cancer, and testicular cancer;

i. cancer of the hematologic system selected from myeloid, acute lymphoblastic leukemia, chronic lymphocytic leukemia, myeloproliferative diseases, multiple myeloma, myelodysplastic syndrome, Hodgkin's disease, and non-Hodgkin's lymphoma;

j. a cancer of the oral cavity selected from lip cancer, tongue cancer, gum cancer, floor of mouth cancer, palate cancer, parotid gland cancer, salivary gland cancer, tonsil cancer, cancer of the oropharynx, cancer of the nasopharynx, pyriform sinus cancer, and cancer of the hypopharynx;

k. a cancer of the skin selected from malignant melanoma, cutaneous melanoma, basal cell carcinoma, squamous cell carcinoma, Karposi's sarcoma, moles dysplastic nevi, lipoma, angioma, dermatofibroma, and keloidal cancer; or l. a cancer selected from cancer of the adrenal glands, neuroblastoma, cancer of connective and soft tissue, cancer of the retroperitoneum and peritoneum, eye cancer, intraocular melanoma, cancer of adnexa, breast cancer, head or/and neck cancer, anal cancer, thyroid cancer, parathyroid cancer, cancer of the adrenal gland, cancer of the endocrine glands and related structures, secondary and unspecified malignant neoplasm of lymph nodes, secondary malignant neoplasm of respiratory and digestive systems, and secondary malignant neoplasm of other sites.

Embodiment 28. A method of treating an autoimmune disorder in a subject in need thereof, the method comprising administering to the subject a therapeutically effective amount of the pharmaceutical composition of any one of Embodiments 1-17.

Embodiment 29. The method of Embodiment 28, wherein the autoimmune disorder rheumatoid arthritis, IgA nephropathy, vascular disease associated with kidney disease, systemic lupus erythematosus (SLE), Wegener's granulomatosis, relapsing polychondritis, atopic dermatitis, psoriasis, sarcoidosis, Behcet's disease, Vogt-Koyanagi-Harada's disease, uveitis, or idiopathic pulmonary fibrosis.

Embodiment 30. A method of treating a microorganism infection in a subject in need thereof, the method comprising administering to the subject a therapeutically effective amount of the pharmaceutical composition of any one of Embodiments 1-17.

Embodiment 31. The method of Embodiment 30, wherein the microorganism infection is caused by virus, bacteria, fungus, or any combination of two or more thereof.

Embodiment 32. A method of treating sepsis and/or septic shock in a subject in need thereof, the method comprising administering to the subject a therapeutically effective amount of the pharmaceutical composition of any one of Embodiments 1-17.

Embodiment 33. A method of treating severe viral-induced pneumonia in a subject in need thereof, the method comprising administering to the subject a therapeutically effective amount of the pharmaceutical composition of any one of Embodiments 1-17.

Embodiment 34. The method of Embodiment 33, wherein the severe viral-induced pneumonia is associated with an infection by a respiratory virus.

Embodiment 35. The method of Embodiment 34, wherein the respiratory virus is selected from an influenza virus, a respiratory syncytial virus, a coronavirus, a rhinovirus, an adenovirus, and a parainfluenza virus.

Embodiment 36. The method of Embodiment 35, wherein the coronavirus is COVID-19.

Embodiment 37. A method of treating mild to severe acute respiratory distress syndrome (ARDS) in a subject in need thereof, the method comprising administering to the subject a therapeutically effective amount of the pharmaceutical composition of any one of Embodiments 1-17, and wherein the subject has positive end-expiratory pressure (PEEP)≥5 cm $H_2O$; and $PaO_2/FiO_2$<300 mm Hg.

Embodiment 38. The method of Embodiment 37, wherein the subject has positive end-expiratory pressure (PEEP)≥5 cm $H_2O$; and $PaO_2/FiO_2$<200 mm Hg.

Embodiment 39. The method of Embodiment 37 or Embodiment 38, wherein the ARDS is associated with an infection by a respiratory virus.

Embodiment 40. The method of Embodiment 39, wherein the respiratory virus is selected from an influenza virus, a respiratory syncytial virus, a coronavirus, a rhinovirus, an adenovirus, and a parainfluenza virus.

Embodiment 41. The method of Embodiment 40, wherein the coronavirus is COVID-19.

Embodiment 42. A method of treating fragile X syndrome in a subject in need thereof, the method comprising administering to the subject a therapeutically effective amount of the pharmaceutical composition of any one of Embodiments 1-17.

Embodiment 43. A method of treating acute lung injury in a subject in need thereof, the method comprising administering to the subject a therapeutically effective amount of the pharmaceutical composition of any one of Embodiments 1-17.

Embodiment 44. The method of Embodiment 43, wherein the lung injury is induced by aspiration, trauma, pancreatitis, blood transfusion, or smoke or toxic chemical inhalation.

Embodiment 45. The method of Embodiment 43, wherein the lung injury is induced by a chemical selected from chlorine, sulfur mustard gas, phosgene, Lewisite, hydrogen chloride, sulfur dioxide, hydrogen sulfide, nitrogen dioxide, ammonia, hydrofluoric acid, ozone, methyl isocyanate, and a combination of two or more thereof.

Embodiment 46. The method of any one of Embodiments 43-45, wherein the lung injury comprises chemical burns, pulmonary edema, laryngeal edema, lung tissue apoptosis, pneumonia, pneumonitis, bronchitis, bronchiolitis, fibrosis, acute respiratory distress syndrome, respiratory tract spasm, or a combination of two or more thereof.

The use of the term "or" in the claims is used to mean "and/or" unless explicitly indicated to refer to alternatives only or the alternatives are mutually exclusive, although the disclosure supports a definition that refers to only alternatives and "and/or."

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions, or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A pharmaceutical composition consisting of a buffered aqueous solution consisting of about 8% w/v to about 13% w/v sulfobutylether-β-cyclodextrin (SBE-β-CD), about 0.08% w/v to about 0.2% w/v ibudilast, disodium phosphate ($Na_2HPO_4$), and sodium dihydrogen phosphate ($NaH_2PO_4$) in water, wherein the pharmaceutical composition is an injectable composition.

2. The pharmaceutical composition of claim 1, wherein the $Na_2HPO_4$ is present in the buffered aqueous solution in an amount of about 0.2% w/v and the $NaH_2PO_4$ is present in the buffered aqueous solution in an amount of about 0.06% w/v.

3. The pharmaceutical composition of claim 1, wherein the SBE-β-CD is present in the buffered aqueous solution in an amount of about 10% w/v.

4. The pharmaceutical composition of claim 1, wherein the ibudilast is present in the buffered aqueous solution in an amount of about 0.1% w/v.

5. A pharmaceutical composition consisting of:

about 10% w/v SBE-β-CD;

about 0.2% w/v disodium phosphate;

about 0.06% w/v sodium dihydrogen phosphate;

about 0.1% w/v ibudilast; and q.s. water;

wherein the pharmaceutical composition is an injectable composition.

6. A method of treating a neurodegenerative disease or disorder in a subject in need thereof, the method comprising administering to the subject a therapeutically effective amount of the pharmaceutical composition of claim 1.

7. A method of treating acute lung injury in a subject in need thereof, the method comprising administering to the subject a therapeutically effective amount of the pharmaceutical composition of claim 1.

8. A method of treating cancer in a subject in need thereof, the method comprising administering to the subject a therapeutically effective amount of the pharmaceutical composition of claim 1.

* * * * *